(12) United States Patent  
Ben-Arie (10) Patent No.: US 9,956,110 B2  
(45) Date of Patent: May 1, 2018

(54) WASHABLE OSTOMY POUCH II

(71) Applicant: Jezekiel Ben-Arie, Chicago, IL (US)

(72) Inventor: Jezekiel Ben-Arie, Chicago, IL (US)

(*) Notice: Subject to any disclaimer, the term of this patent is extended or adjusted under 35 U.S.C. 154(b) by 540 days.

(21) Appl. No.: 14/453,714

(22) Filed: Aug. 7, 2014

(65) Prior Publication Data

US 2015/0018789 A1   Jan. 15, 2015

Related U.S. Application Data

(63) Continuation-in-part of application No. 14/304,909, filed on Jun. 14, 2014.

(60) Provisional application No. 61/838,230, filed on Jun. 22, 2013.

(51) Int. Cl.
| | |
|---|---|
| *A61F 5/442* | (2006.01) |
| *A61F 5/44* | (2006.01) |
| *A61F 5/443* | (2006.01) |
| *A61F 5/445* | (2006.01) |

(52) U.S. Cl.
CPC .............. *A61F 5/442* (2013.01); *A61F 5/443* (2013.01); *A61F 5/445* (2013.01); *A61F 5/4405* (2013.01); *A61F 5/4407* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,520,831 | A * | 8/1950 | Chincholl | A61F 5/445 604/335 |
| 2,782,785 | A * | 2/1957 | Arcand | A61F 5/445 604/334 |
| 3,690,320 | A * | 9/1972 | Riely | A61F 5/4407 604/333 |
| 3,815,794 | A * | 6/1974 | Carlisle | B65D 75/5822 222/107 |
| 3,865,109 | A * | 2/1975 | Elmore | A61F 5/441 604/339 |
| 3,897,780 | A * | 8/1975 | Trousil | A61F 5/445 604/344 |
| 4,233,977 | A * | 11/1980 | Mattson | A61F 5/4407 604/335 |
| 4,372,308 | A * | 2/1983 | Steer | A61F 5/441 604/333 |

(Continued)

*Primary Examiner* — Todd J Scherbel
*Assistant Examiner* — Guy K Townsend (57) ABSTRACT

A washable ostomy pouch configured for accumulating discharged waste and also for draining and washing it without detaching the pouch from the user. The washable pouch has a draining duct and a washing duct which is elevated above the waste level and enables pouring water without waste overflow. The washable pouch has a flat structure. Both the washing and draining ducts have seals. The washing duct has a funnel shape which facilitates pouring water into the pouch, whereby liquefying the discharged waste and enabling easier draining. The abdominal inlet coupling can detachably secure the washable pouch to a snugly fitting abdominal adhesive faceplate coupling which is attached to an abdominal adhesive faceplate that is configured to adhere to the user's abdominal skin surrounding the user's stoma. This allows the user to replace the pouch multiple times without having to detach the abdominal adhesive faceplate.

10 Claims, 8 Drawing Sheets

(56) References Cited

U.S. PATENT DOCUMENTS

| | | | | |
|---|---|---|---|---|
| 4,403,991 A | * | 9/1983 | Hill | A61F 5/443 604/337 |
| 4,465,486 A | * | 8/1984 | Hill | A61F 5/443 24/30.5 R |
| 4,654,037 A | | 3/1987 | Fenton | |
| 4,692,159 A | | 8/1987 | Kuzemchak | |
| 4,755,177 A | * | 7/1988 | Hill | A61F 5/443 604/336 |
| 4,863,447 A | * | 9/1989 | Smith | A61F 5/441 251/323 |
| 4,941,878 A | | 7/1990 | Petrik | |
| 5,037,408 A | * | 8/1991 | Henry | A61F 5/445 604/332 |
| 5,470,325 A | | 11/1995 | Fundock | |
| 5,503,633 A | | 2/1996 | Saunders | |
| 5,941,640 A | * | 8/1999 | Thatcher | A45F 3/20 383/22 |
| 6,171,288 B1 | * | 1/2001 | Wiltshire | A61F 5/441 604/333 |
| 6,224,581 B1 | | 1/2001 | Withers | |
| 6,267,506 B1 | * | 7/2001 | Campion | A45C 11/22 224/148.2 |
| 6,336,918 B1 | * | 1/2002 | Olsen | A61F 5/4407 604/332 |
| 6,582,410 B1 | | 6/2003 | Rutman | |
| 6,644,854 B2 | * | 11/2003 | Lien | A45F 3/20 222/175 |
| D501,399 S | * | 2/2005 | Tobolka | A61F 5/44 D9/434 |
| 6,918,898 B2 | | 7/2005 | King | |
| D607,559 S | * | 1/2010 | Schena | A61F 5/44 D24/118 |
| D618,791 S | * | 6/2010 | Schena | A61F 5/44 D24/118 |
| 7,879,015 B2 | * | 2/2011 | Villefrance | A61F 5/4405 604/332 |
| 7,879,016 B2 | * | 2/2011 | Mandzij | A61F 5/4407 4/144.1 |
| 7,918,836 B2 | | 5/2011 | Gill | |
| 8,016,802 B1 | | 9/2011 | Schena | |
| 8,167,857 B2 | | 1/2012 | James | |
| 2006/0079854 A1 | * | 4/2006 | Kay | A61F 5/4405 604/328 |
| 2006/0106354 A1 | | 5/2006 | Vantroostenberghe | |
| 2006/0111682 A1 | * | 5/2006 | Schena | A61F 5/4407 604/334 |
| 2006/0155252 A1 | | 7/2006 | Walker | |
| 2006/0253090 A1 | * | 11/2006 | Bradley | A61F 5/4405 604/334 |
| 2008/0060679 A1 | | 3/2008 | Rosenberg | |
| 2009/0163885 A1 | | 6/2009 | Pedersen | |
| 2015/0018789 A1 | * | 1/2015 | Ben-Arie | A61F 5/442 604/334 |
| 2015/0065970 A1 | * | 3/2015 | Ben-Arie | A61F 5/442 604/333 |

* cited by examiner

WASHABLE OSTOMY POUCH II

CROSS-REFERENCE TO RELATED APPLICATIONS

This Application is Continuation in Part of application Ser. No. 14/304,909 Filed on Jun. 14, 2014
This application claims the benefit of a provisional patent application: Ser. No. 61/838,230 filed on 22 Jun. 2013

FEDERALLY SPONSORED RESEARCH

Not Applicable

SEQUENCE LISTING OR PROGRAM

Not Applicable

BACKGROUND OF THE INVENTION

Field of the Invention

The invention is in the area of ostomy pouches.
The Problems in Draining Ostomy Pouches
Drainable pouches are being used by people who underwent ileostomy also referred to as ostomy. Ostomy is the construction of an artificial opening from the ileum through the abdominal wall, permitting drainage of the contents of the small intestine. The drainable pouch is attached to the abdominal opening and collects the discharged waste drained from the small intestine. Every few hours the pouch is filled and needs to be drained. Usually these pouches have the shape of a bag and are made of flexible material such as plastic sheets. The pouch's inlet is attached to the abdominal opening (also called stoma) usually by an abdominal inlet coupling which can detachably secure the washable pouch to an abdominal adhesive faceplate. The abdominal adhesive faceplate has on its proximal side an adhesive layer called skin barrier surrounding a central opening. The adhesive layer of skin barrier enables to adhere said abdominal adhesive faceplate to the user's abdominal skin surrounding the user's stoma. There is a second type of drainable pouches which have an abdominal inlet which is connected directly to the abdominal adhesive faceplate without a detachable coupling.

Prevalent pouches also have an outlet from which the pouch is being drained. This outlet is sealed during discharged waste accumulation and can be opened for drainage and re-sealed afterwards. When the user drains the pouch, the user has to open the outlet and to squeeze the pouch in order to drain ft. The inventor personally had ileostomy and had been using these pouches for few years. Users of ostomy pouches are experiencing a major difficulty in the draining process. Since the discharged waste is highly viscous and sticky, it adheres to the inner walls of the pouch and draining it requires a lot of squeezing. Even after a lot of squeezing the pouch is not completely emptied and remains with considerable residue inside. To alleviate this problem, the inventor developed a washing and draining procedure in which the user is adding water to the pouch through the draining outlet. Next, the user mixes the discharged waste with the water into a fluent mixture, and then drains the mixture via the outlet. This process needs repeating 2-3 times until the pouch is entirely cleaned. It was found that this washing procedure is faster, easier, more hygienic and achieves much better drainage. Notice that the whole procedure does not require detaching the pouch from the stoma.

Prior Art

Searching the PTO database for inventions which employ various means for washing pouches yielded several patents and patent applications. But all of them were entirely dissimilar to our invention. Several patent applications propose various methods for flushing ostomy pouches. In US 20080060679 Rosenberg proposes to use a special flushing water container which connects to the pouch's outlet. Rosenberg claims no water spills but since the outlet is located at the bottom of the pouch, it presents a major problem how to disconnect the container without spilling. In addition, this arrangement requires special installation in every toilet used.

In U.S. Pat. No. 4,692,159 Kuzemchak invents a flushing nozzle which fits the pouch's inlet and which connects to a water pipe. However, it seems that Kuzemchak forgot that this inlet is connected to the user's abdominal opening and removing the pouch when it is filled with discharged waste is almost impossible without spilling. Very similar approaches are presented in U.S. Pat. No. 6,224,581 by Withers et al. and in US 20060155152 by Walker.

In U.S. Pat. No. 6,582,410 Rutman invents an ostomy drainage apparatus which consists of a tube which connects the pouch's outlet to a large container. We fail to see how this is better than simply draining the pouch directly to a toilet bowl.

In U.S. Pat. No. 4,941,878 Petrik invented an ostomy pouch flasher which is basically a metal pipe with few holes at its end and a water pipe inlet at its other end. This pipe is designed to be inserted into the pouch and help flushing it.

In US 2006/0106354 A1 Vantrustenberge invents an ostomy pouch with 3 openings. The first one serves as an inlet which is connected to the user's abdominal opening (stoma). The second one is a wide pouch outlet which is used for pouch draining. The third opening in the pouch is a port connected to a one way valve which has a stem pipe at the valve's outlet. The third opening has two uses. The first use is for expelling gases accumulated in the pouch wherein the valve is activated by pressing the pouch and creating enough pressure which opens the one directional valve and allowing the gas to exit. The second use of the third opening is to use it for flushing the bag after draining. The stem pipe is connected to a water source and water is being forced into the pouch. This invention has two major flaws. The first one is the need for a pressurized water source that needs to be connected to the stem pipe for flushing. The second problem is a contradiction in the invention design because if the one way valve is designed to expel gasses from the pouch outwards it will block any flow of rinsing water inwards into the pouch. A similar invention is presented by King in U.S. Pat. No. 6,918,898 B2. King uses an enema bag as an irrigation water source which is connected by a tube to a plapped opening in the pouch. In our opinion, enema's dripping is much too slow for pouch rinsing and a flapped input will allow likage of gasses and waste from the pouch.

Schena in U.S. Pat. No. 8,016,802 B1 invented a pouch irrigator which consists of a curved porous pipe (called manifold by the inventor) installed inside the pouch. Schena is manufacturing his invention under the name EZ-Clean. The irrigator has a pipe inlet installed at a pouch's opening. This invention is not practical because it requires a pressurized water source connected to the irrigator's inlet. Thus, the user can use Schena's invention only in toilets with appropriate water source. It is also very expensive solution for a disposable pouch because the manifold needs to be disposed with the pouch every few days. Another disadvantage of Schena's pouch is that it is quite bulky under the clothes. A similar pouch irrigator composed of a porous pipe installed inside the pouch was invented by Fenton in U.S. Pat. No. 4,654,037. Similar invention with pipe irrigation is in U.S. Pat. No. 7,918,836 B2 by Gill et al.

An ostomy suction system was invented by James in U.S. Pat. No. 8,167,857 B2, which uses vacuum tube connected to the pouch outlet for efficient draining.

Fundock in U.S. Pat. No. 5,470,325 invented an irrigation and venting assembly which is composed of a simple pipe inlet installed on the top of the pouch. The pipe inlet needs to be connected to a water source for rinsing.

An ostomy bag cleaning apparatus is described in U.S. Pat. No. 5,503,633 by Saunders. The apparatus is actually a drainage construction which enables to flush used ostomy pouches with a water sprinkler over the toilet. Similar approach to pouch cleaning is in US 2006/0237039 A1 by Sarvis. An peelable ostomy bag which can be cleaned by peeling it from the abdominal opening is invented by Pedersen et al. in US 2009/0163885 A1.

BRIEF SUMMARY OF THE INVENTION

Our invention pertains to a novel pouch structure which enables easy washing and draining of ostomy pouches without detaching the pouch from the user. Usually, ostomy pouches are made of flexible material such as plastic and have an inlet opening which is attached to the abdominal opening of the user (stoma). The pouch accumulates the discharged waste excreted from the abdominal opening. Every few hours the pouch is filled and needs to be drained. Usually pouches have an outlet from which the pouch is being drained. This outlet is sealed most of the time when discharged waste is being accumulated and can be opened for drainage and re-sealed afterwards. When the user drains the pouch, the user has to open the outlet and to squeeze the pouch in order to force out the discharged waste. Users are experiencing a major difficulty in such draining process since a is messy and inefficient. The discharged waste is highly viscous and sticks to the pouch walls. Large portions of the discharged waste still remain in the pouch even after a lot of squeezing. Few inventions (described in the previous section) propose to improve the drainage by mixing the discharged waste with water, which converts it to more fluent mixture that can be easier to drain. These inventions propose to add water to the pouch via various structures of pipe inlets installed in the pouch. There are two major problems with these approaches which renders them impractical. Firstly, pipe inlets need to be connected to a water source via a flexible pipe. This requirement limits the usage of such pouches only to special toilets with a water source and fitting pipes. Since most toilets are not equipped with such water sources, users of pouches with pipe inlet can use them only in specially equipped locations. Even more serious problem arises from the requirement to include in each pouch an inner pipe with a pipe inlet connection. Adding a pipe structure to each pouch makes it quite bulky and expensive since ostomy pouches need to be worn under the clothes and replaced with new ones every few days.

Our invention proposes an economical and efficient solution to draining and washing pouches by adding an additional washing duct inlet at the top of the pouch. This solution is quite economical because such a washing duct inlet can be constructed from the same flexible material as the rest of the pouch and could have the same sealing arrangement as the pouch's draining duct outlet. The invention also enables efficient drainage and washing because it does not require any special water source and the washing duct inlet, which could have a funnel shape can be filled from a variety of water vessels and containers. Since the proposed washing duct inlet is located at the top of the pouch and the draining duct outlet is located at the bottom of the pouch, the washing and rinsing process is quite efficient. Pouring water into the washing inlet on top rinses, washes and drains the solid waste more efficiently downwards through the draining duct outlet, which is located at the bottom of the pouch. To facilitate water input, the washing duct inlet could have a shape of a funnel. In order to separate the funnel from the waste, usually accumulated in the pouch, the funnel is installed on top of a washing duct protruding from the top of the pouch. This waste free protruding washing duct also enables to install an air filter in an opening in the washing duct's wall. Air filters installed even on top of the central cavities of conventional pouches are not separated enough from the waste and are getting clogged very quickly. The washing duct inlet is also equipped on its very top with a washing duct seal to prevent accidental leakage from the washing duct inlet.

Another advantage of the washable pouch described in this application is its very flat structure which is relatively cheap to manufacture. The pouch including the washing duct inlet, the abdominal inlet and the draining duct outlet is manufactured by fusing two flat sheets (henceforth called front wall and rear wall) of flexible material at their perimeter margins all around their outer boundaries (i.e. perimeters) except for two short perimeter segments for openings for the upper washing duct opening and for the lower draining duct opening. The walls have identical two dimensional shapes except for an opening in the rear wall for the abdominal inlet. The two dimensional shape of the walls includes a central area for the pouch central cavity and two protruding extensions which extend from the central area which are configured for the washing duct and for the draining duct. The width of these extensions is substantially smaller than the width of the central area which is configured for the central cavity, which requires much larger volume in order to store all the waste. The walls are fused at their margins all along their perimeter and the only places the walls are not fused are short perimeter segments located at the openings necessary for the upper washing duct opening and the lower draining duct opening. The pouch's flat structure is not conspicuous when the user wears the pouch under the user's clothes. Other inventions which employ various configurations of rinsing pipes are much more bulky and expensive in manufacturing.

Our invention has a wide funnel shaped washing duct which enables the user to rinse the pouch using a variety of water sources. Our inlet also has a washing duct seal which enables to seal the washing duct when not in use. Expulsion of excess gases which are discharged by the waste and accumulated at the top of the pouch can also be achieved simply by momentarily opening the washing duct seal and sealing it afterwards. Installing a washing duct on top has additional advantages. In our embodiment, we propose to install in an opening in the washing duct's wall an air filter that enables to remove excess gasses discharged from the solid waste. Usually such filters are installed at the upper side of other prevalent pouches, but such filters are not separated enough from the waste and become clogged with solid waste even after a very short use. Such clogging effectively blocks the filter and renders it useless. Whereas, installing a filter on the washing duct's wall separates it more effectively from the solid waste in the pouch because the washing duct extends from the very top of the pouch. Other problems that are routinely encountered by users of ostomy pouches are skin wounds and irritation, which are caused by the sharp edges of the adhesive layer which adheres the abdominal adhesive faceplate to the abdominal skin around the abdominal opening (stoma). For some reason, this adhesive layer of skin barrier, which comprises of a disc made of adhesive material, has sharp edges on its circumference. The user could have avoided many irritations and wounds if these sharp edges would have been tapered or rounded at the perimeter of the adhesive layer. For this reason, we propose in our embodiment to taper the edges of the adhesive material. In summation, our invention is entirely different from all the inventions described above because our invention has a protruding washing duct installed on top of the pouch's central cavity. Our invention is the only one which has a wide funnel shaped inlet at the top of a protruding washing duct which enables to rinse the pouch manually using water from any container, bottle or pitcher.

Our washable pouch has another important feature. The washable pouch can be detachably secured to the abdominal adhesive faceplate which is adhered to the abdominal skin surrounding the stoma. The distal side of the abdominal adhesive faceplate is connected to a abdominal adhesive faceplate coupling. The abdominal adhesive faceplate coupling is composed of a three dimensional multi-ring structure which snugly fits a three dimensional multi-ring structure of the abdominal inlet coupling, which is an integral part of the washable pouch. The three dimensional multi-ring structure of the abdominal adhesive faceplate coupling and the three dimensional multi-ring structure of the abdominal inlet coupling form a secure, watertight coupling when coupled together which enable the user's discharged waste to flow from the stoma to the washable pouch without any leakage. This coupling can be detached by pulling the multi-ring structure of the abdominal adhesive faceplate coupling away from the multi-ring structure of the abdominal inlet coupling. However, the user does not need to detach the coupling when the pouch is washed.

DETAILED DESCRIPTION OF THE INVENTION AND DRAWINGS

Figure 1:
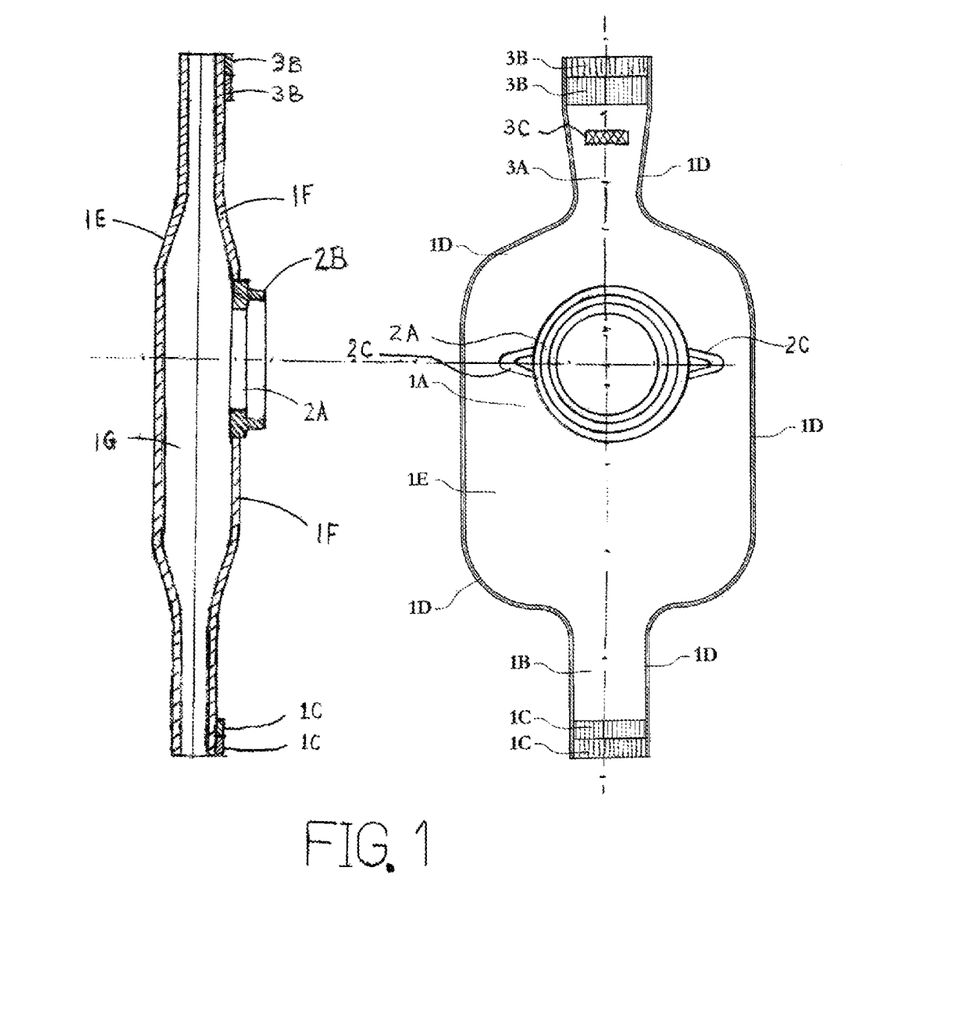
FIG. 1 describes the rear view of an embodiment of the washable pouch 1A and cross section of the pouch's side view. The rear view depicts the rear flexible wall 1F with the adhesive abdominal inlet coupling 2B.

FIG. 1 describes a rear view of an embodiment of the washable pouch 1A. The rear flexible wall 1F is illustrated with the abdominal inlet coupling 2B and the abdominal inlet opening 2A. The abdominal inlet coupling 2B which surrounds the abdominal inlet opening 2A has a special three dimensional multi-ring structure which snugly fits the three dimensional multi-ring structure of the abdominal adhesive faceplate coupling 8A (shown in FIG. 2). The three dimensional multi-ring structure 2B and three dimensional multi-ring structure 8A form a secure, watertight coupling when coupled together which enable the user's discharged waste to flow from the stoma to the washable pouch without any leakage. This coupling can be detached by pulling the three dimensional multi-ring structure 8A of the faceplate coupling away from the three dimensional multi-ring structure 2B of the abdominal inlet coupling.

However, the user does not need to detach the coupling when the pouch is washed.

The abdominal inlet coupling 2B has two eyelets 2C which facilitate fastening the washable pouch more securely to the user's abdomen. At the bottom of pouch 1A is a draining duct 1B for draining the accumulated discharged waste. The draining duct 1B can be sealed by the draining duct seal 1C by folding and adhering the two 1C interlocking type strips together one against the other. The pouch has also a washing duct 3A, which is installed at the top of the pouch 1A. The washing duct 3A has a shape of a funnel which facilitates pouring water into the pouch 1A. The washing duct 3A also has a washing duct seal 3B which enables to seal it when not in use by folding and adhering together the two interlocking type strips 3B In addition, the washing duct 3A also could have an optional air filter 3C, which is installed at an opening in the wall of the washing duct 3A. The rear flexible wall 1F is fused to the front flexible wall 1E all along their perimeter margins 1D except for two short perimeter segments for the upper washing duct opening of the washing duct 3A and the lower draining duct opening 1B. The fused strip 1D is shown as a wide hashed line in FIG. 1. The walls 1E and 1F are made of flexible planar sheets and have an identical two dimensional shapes except for the abdominal inlet opening 2A in 1F. The central area of the two dimensional shapes 1E and 1F which is configured for the pouch's central cavity, has two protruding extensions 1B and 3A configured for the draining duct and the washing duct respectively. The side view cross section in FIG. 1 shows that the central area of the pouch corresponds to a central cavity 1G which is formed between the two walls 1E and 1F. The central cavity 1G provides the pouch with a space for discharged waste accumulation.

Figure 2:
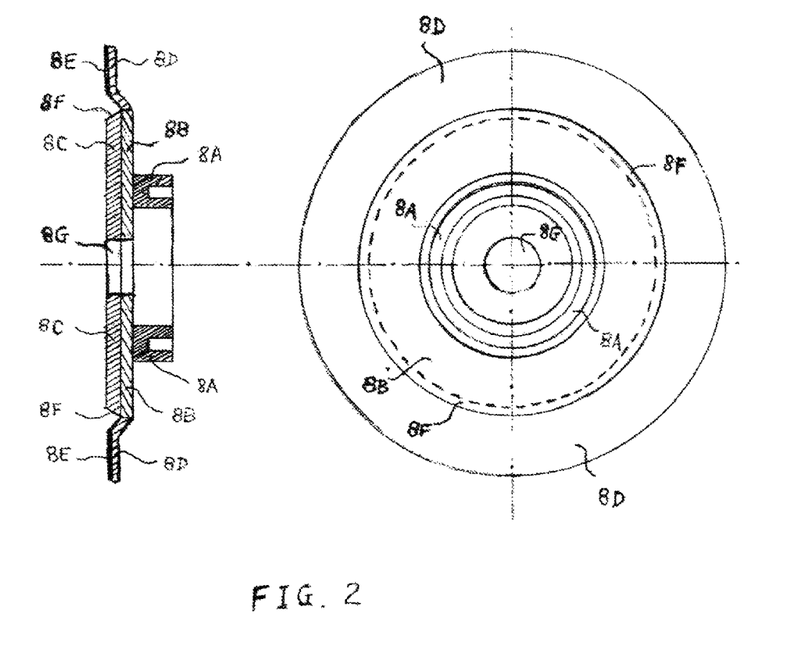
FIG. 2 depicts a frontal view and a cross section side view of the abdominal adhesive faceplate 8B with its abdominal adhesive faceplate coupling 8A. The faceplate 8B has on its proximal side (body side) an adhesive layer of skin barrier 8C surrounding a central opening 8G.

FIG. 2 illustrates the front view and the side view cross section of the abdominal adhesive faceplate 8B. The abdominal adhesive faceplate 8B is attached to a abdominal adhesive faceplate coupling 8A which has a shape of a three dimensional multi-ring structure which snugly fits the three dimensional multi-ring structure 2B (shown in FIG. 1) which is a part of the abdominal inlet coupling 2B of the washable pouch. The abdominal adhesive faceplate 8B has a shape of a rigid disk. The abdominal adhesive faceplate 8B has on its proximal side (body side) an adhesive layer of skin barrier 8C surrounding a central opening 8G configured for the stoma. The adhesive layer of skin barrier 8C is designed to adhere to the user's abdominal skin around the stoma. The adhesive layer of skin barrier 8C has a tapered circumference (perimeter) 8F designed to reduce abdominal skin irritation caused by sharp edges on the perimeter of the adhesive layer of skin barrier 8C. A flexible circular strip 8D is attached to the circumference of the abdominal adhesive faceplate 8B. The flexible circular strip 8D has a glue layer 8E which is designed to adhere the abdominal adhesive faceplate circumference to the abdominal skin surrounding the adhesive layer of skin barrier 8C of the abdominal adhesive faceplate and to strengthen the abdominal adhesive faceplate adherence of the adhesive layer of skin barrier 8C to the user's abdominal skin.

Figure 3:
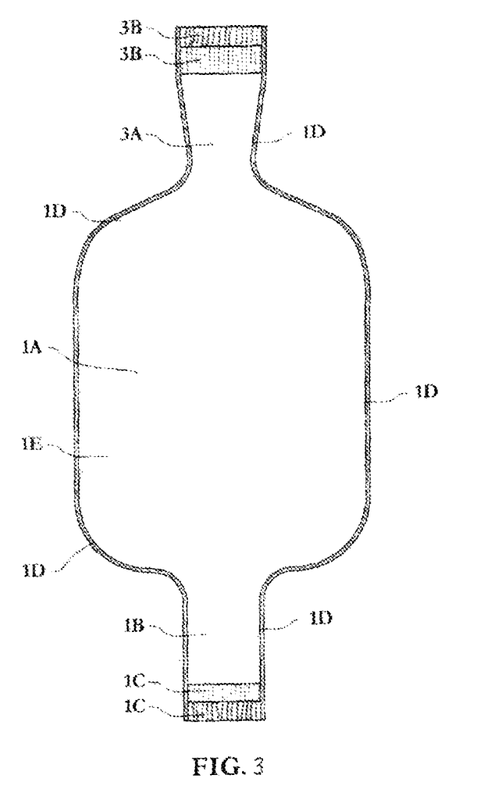
FIG. 3 illustrates the front view of an embodiment of the washable pouch 1A in which the front flexible wall 1E is shown.

FIG. 3 illustrates the front view of an embodiment of the washable pouch 1A. The front flexible wall 1E has a central area configured for the central cavity 1G and two protruding extensions 3A and 1B configured for a protruding washing duct 3A and for a protruding draining duct 1B. The front flexible wall 1E is fused all along its perimeter 1D to the rear flexible wall 1F except for two short perimeter segments configured for the upper washing duct opening 3A and the lower draining duct opening 1B. The fusing strip 1D is shown as a wide dark line as well. The washing duct 3A has a washing duct seal 3B which enables to block all flow through the washing duct 3A when the washing duct seal 3B is sealed by folding and adhering its two interlocking type strips 3B one against the other. Similarly, the draining duct 1B has a draining duct seal 1C which enables to block all flow through the draining duct 1B when the draining duct seal 1C is sealed by folding and adhering its two interlocking type strips 1C one against the other.

Figure 4:
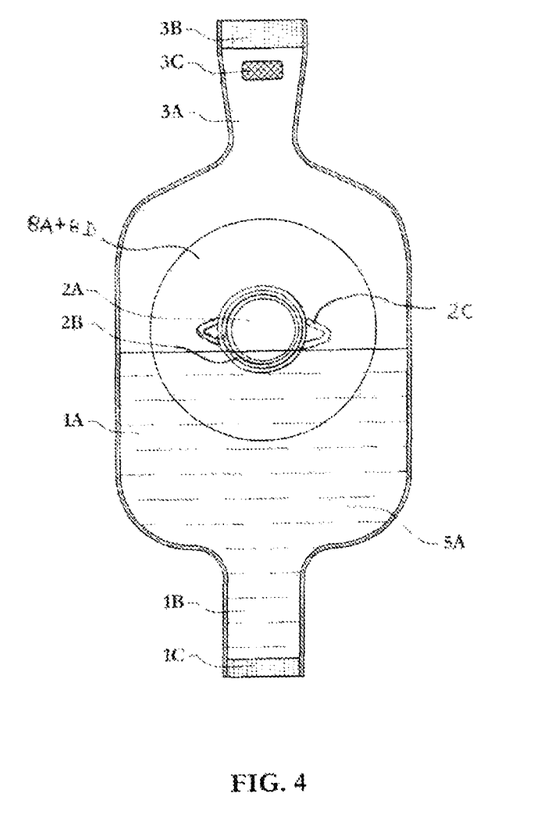
FIGS. 4-8 describe a proposed washing and draining procedure of the pouch.

FIGS. 4-8 describe a proposed draining and washing procedure using the drainable and washable pouch 1A. In order to illustrate the different states of the contents in the washable pouch during washing and draining, FIGS. 4-8 show the washable pouch as if it was made of transparent walls 1E and 1F. FIG. 4 describes the pouch 1A in the accumulation phase when both the draining duct 1B and the washing duct 3A are sealed and the discharged waste 5A which is excreted from the user's stoma via the abdominal inlet opening 2A is accumulated in the washable pouch 1A.

Figure 5:
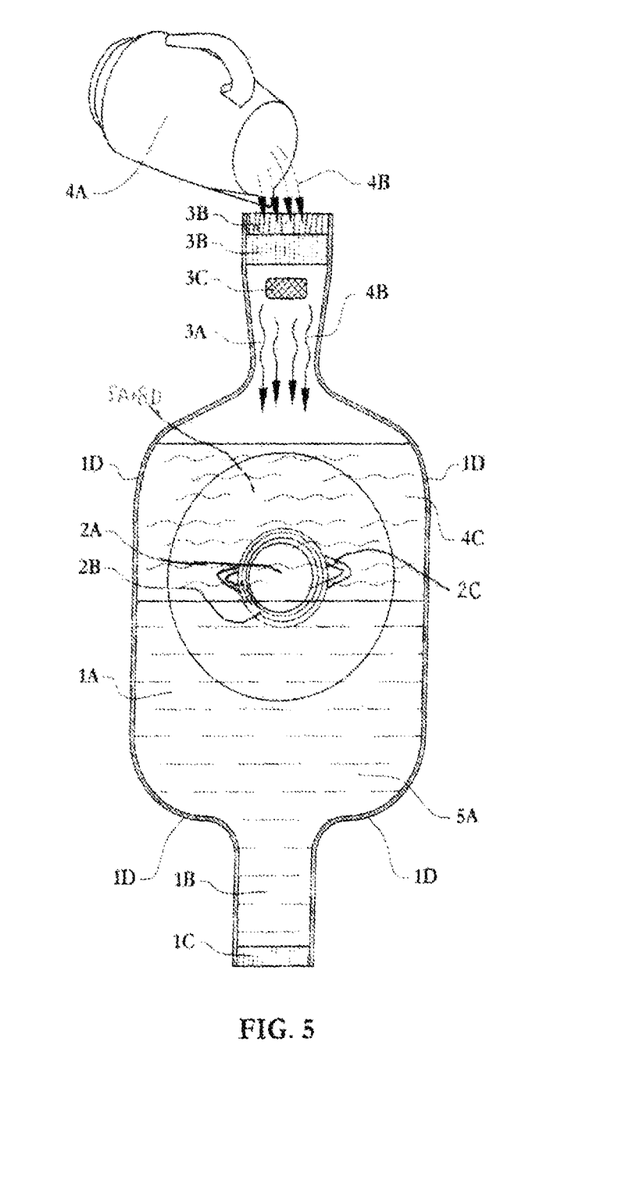

When the user decides to drain the washable pouch 1A, the user opens the washing duct seal 3B of the washing duct 3A and pours water 4B into the washing duct 3A from the pitcher 4A. This step is illustrated in FIG. 5. The amount of water 4C which is poured from the pitcher 4A should be sufficient to create a fluent mixture with the accumulated discharged waste 5A in the washable pouch 1A. The draining duct seal 1C of the draining duct 1B is sealed during this phase.

Figure 6:
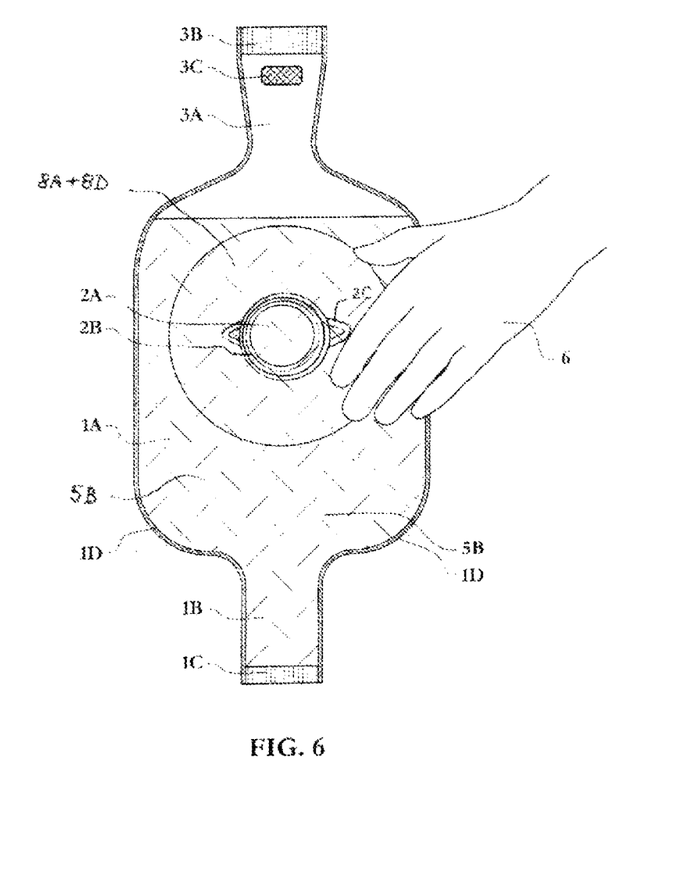

As illustrated in FIG. 6, the user then seals the washing duct 3A and squeezes the washable pouch 1A with the user's hands 6 several times until the water mixes with the discharged waste and creates a fluent mixture 5B. The squeezing and mixing step is described in FIG. 6. The draining duct seal 1C of the draining duct 1B remains closed at this phase.

Figure 7:
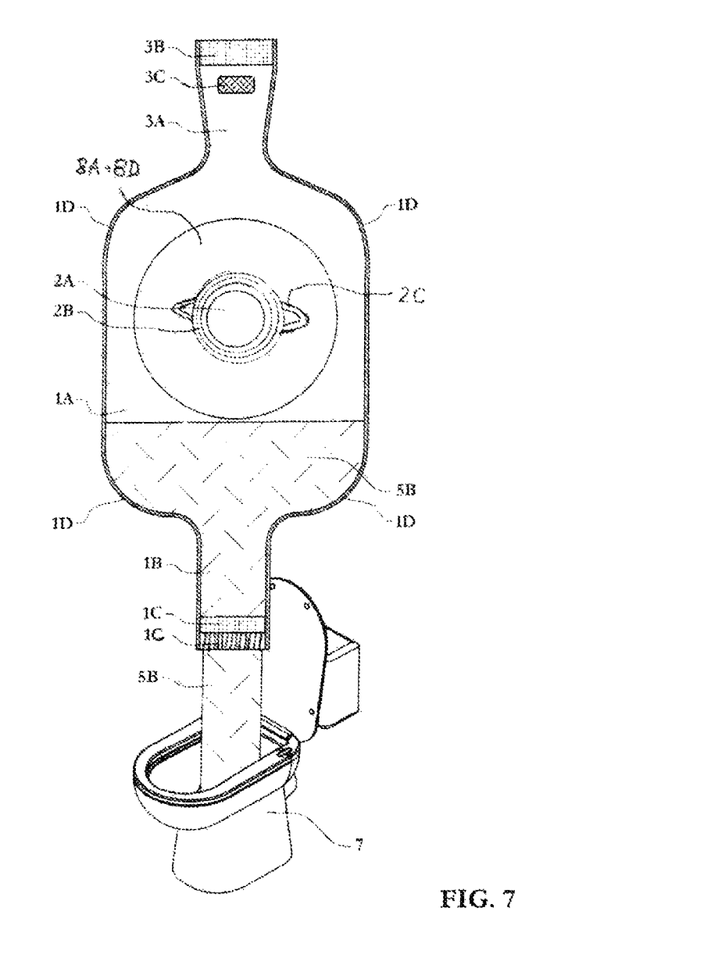
Figure 8:
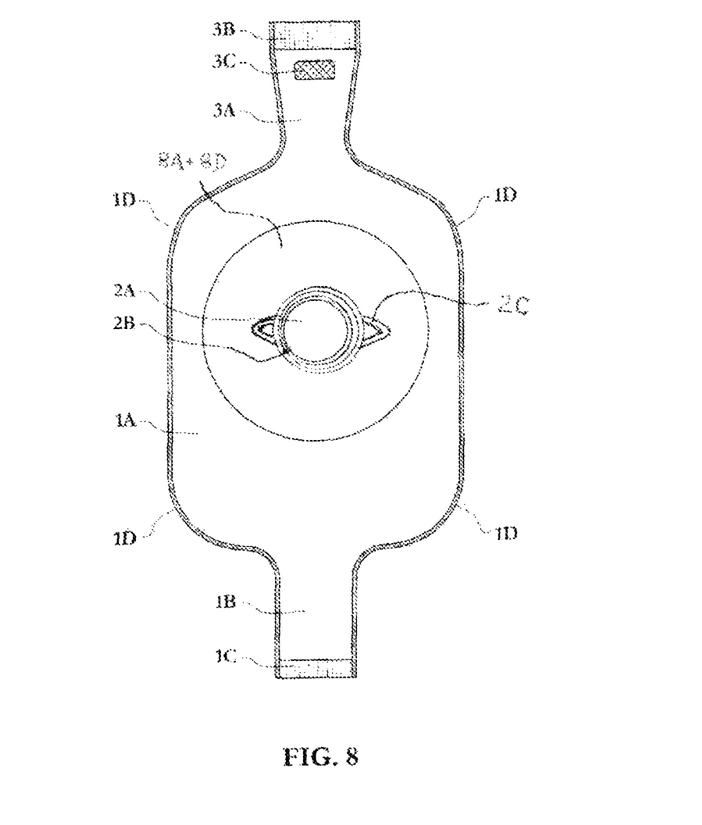

In FIG. 7, the user opens the draining duct seal 1C and drains the mixture 5B into the toilet bowl 7. The washing duct seal 3B remains closed at this phase. FIG. 8 describes the state of the washable pouch 1A after drainage is completed. The draining duct 1B and the washing duct 3A are sealed by seals 1C and 3B respectively. At this stage the pouch is ready for the next discharged waste accumulation.

In our experience, almost all the discharged waste mixture 5B is drained at the first washing. If some discharged waste still remains in the washable pouch 1A, the user can repeat the washing procedure until the pouch is completely emptied.

What is claimed is:

1. A washable ostomy appliance configured to attach to a user in order to accumulate discharged waste and to be washed and drained without being detached from said user; the washable ostomy appliance comprising:
    a washable pouch comprising:
        a central cavity,
        a front wall,
        a rear wall,
        an abdominal inlet opening,
        an abdominal inlet coupling,
        an abdominal adhesive faceplate,
        a draining outlet situated at a lower end of said central cavity and fluidly connected with said central cavity,
        a washing inlet situated at an upper end of said central cavity and fluidly connected with said central cavity,
        a washing duct, and
        a draining duct;
        said washing duct comprising: a washing duct wall,
        a lower washing duct opening situated at a lower end of the washing duct,
        a washing duct seal situated at a top of the washing duct and
        an upper washing duct opening situated at an upper end of the washing duct seal;
        wherein said lower washing duct opening is attached to and fluidly connected with said washing inlet;
        wherein said washing duct maximal horizontal width is substantially smaller than the maximal horizontal width of the central cavity;
        said draining duct comprising: a draining duct wall,
        an upper draining duct opening situated at an upper end of the draining duct,
        a draining duct seal situated at a bottom of said draining duct and
        a lower draining duct opening situated at a lower end of said draining duct seal;
        wherein said upper draining duct opening is attached to and fluidly connected with said draining outlet;
    wherein said central cavity is fluidly connected to: said abdominal inlet opening, to said lower washing duct opening via said washing inlet and to said upper draining duct opening via said draining outlet;
    wherein the central cavity is situated between said front wall and said rear wall;
    wherein said abdominal inlet opening is situated in said rear wall;
    wherein said abdominal inlet opening is surrounded by said abdominal inlet coupling, which is attached to said rear wall;
    wherein said abdominal inlet coupling has a first three dimensional structure;
    wherein said front wall and said rear wall are made of planar sheets made of flexible material;
        wherein said front wall and said rear wall are fused together at their perimeters except for a lower perimeter segment configured for the lower draining duct opening and an upper perimeter segment configured for the upper washing duct opening;
        wherein, said abdominal adhesive faceplate comprising: a distal side and a proximal side; wherein said abdominal adhesive faceplate also comprises a rigid plate;
    wherein said distal side comprising an abdominal adhesive faceplate coupling which has a second three dimensional structure which is configured to fit snugly to said first three dimensional structure of said abdominal inlet coupling;
    wherein, the first three dimensional structure is configured to detachably secure said second three dimensional structure just by a snug fitting without using an adhesive material;

whereby, said abdominal adhesive faceplate coupling is configured to detachably couple and secure said abdominal inlet coupling;

wherein, said proximal side comprises an adhesive layer of a skin barrier surrounding a central opening of the abdominal adhesive faceplate; wherein said abdominal inlet opening is fluidly connected to said central opening when the abdominal adhesive faceplate coupling is coupled with the abdominal inlet coupling; wherein said central opening is configured to encircle an user's stoma;

wherein said adhesive layer of the skin barrier is configured to adhere said abdominal adhesive faceplate to an user's abdominal skin surrounding said user's stoma;

whereby, said washable pouch is attached to said user's abdominal skin surrounding said user's stoma when said abdominal adhesive faceplate coupling is secured to said abdominal inlet coupling;

whereby, said washable pouch is detached from said user's abdominal skin surrounding said user's stoma when said abdominal adhesive faceplate coupling is detached from said abdominal inlet coupling;

whereby, said washable pouch can be detached from said user and re-attached to said user multiple times while said abdominal adhesive faceplate remains adhered to said user.

2. The washable ostomy appliance of claim 1, wherein said proximal side further comprises a circular flexible adhesive strip, which surrounds and also is attached to said abdominal adhesive faceplate;

wherein, said circular flexible adhesive strip is configured to adhere to said user's abdominal skin surrounding said adhesive layer of the skin barrier.

3. The washable ostomy appliance of claim 1, wherein said adhesive layer of the skin barrier has a tapered perimeter that is configured to reduce irritation of said user's abdominal skin when applied thereto.

4. The washable ostomy appliance of claim 1, wherein said abdominal inlet coupling has at least one eyelet which is configured to facilitate fastening said washable pouch to said user's body.

5. The washable ostomy appliance of claim 1, wherein an air filter is installed in an opening in said washing duct wall.

6. The washable ostomy appliance of claim 1, wherein the washing duct wall has a shape of a funnel, wherein said upper washing duct opening of said washing duct wall is configured to be wider than said lower washing duct opening in both: (i) an open position when the washing duct seal is open; and (ii) a closed position when the washing duct seal is closed, such that the washing duct wall is configured to facilitate pouring of water into the upper washing duct opening when the upper washing duct opening is in said open position.

7. The washable ostomy appliance of claim 1, wherein said second three dimensional structure of said abdominal adhesive faceplate coupling has a second three dimensional structure of multiple concentric raised and depressed circular rings which is configured to snugly fit and detachably secure a first three dimensional structure of multiple concentric raised and depressed rings of the first three dimensional structure of the abdominal inlet coupling without using said adhesive material.

8. The washable ostomy appliance of claim 1, wherein the draining duct seal comprises a first multiplicity of interlocking strips of said draining duct wall that are configured to seal the lower draining duct opening by folding the draining duct wall such that the first multiplicity of interlocking strips are adhered to each other to seal the lower draining duct opening; and wherein the washing duct seal comprises a second multiplicity of interlocking strips of said washing duct wall that are configured to seal the upper washing duct opening by folding said washing duct wall such that the second multiplicity of interlocking strips are adhered to each other to seal the upper washing duct opening.

9. The washable ostomy appliance of claim 1, wherein said draining duct seal comprises a first multiplicity of joining strips of said draining duct wall and a first multiplicity of non-resilient bars that are configured to seal said lower draining duct opening by folding the draining duct wall and securing said first multiplicity of joining strips to each other using said first multiplicity of non-resilient bars;

said washing duct seal comprises a second multiplicity of joining strips of said washing duct wall and a second multiplicity of non-resilient bars that are configured to seal the upper washing duct opening by folding the washing duct wall and securing said second multiplicity of joining strips to each other using said second multiplicity non-resilient bars.

10. The washable ostomy appliance of claim 1, wherein said proximal side has a rigid convex shape; wherein said abdominal adhesive faceplate and said adhesive layer of the skin barrier also have said rigid convex shape.

* * * * *